US005827840A

United States Patent [19]
Ramamurthy et al.

[11] Patent Number: 5,827,840
[45] Date of Patent: Oct. 27, 1998

[54] PROMOTION OF WOUND HEALING BY CHEMICALLY-MODIFIED TETRACYCLINES

[75] Inventors: Nungavaram S. Ramamurthy; Lorne M. Golub, both of Smithtown; Thomas F. McNamara, Port Jefferson, all of N.Y.

[73] Assignee: The Research Foundation of State University of New York, Albany, N.Y.

[21] Appl. No.: 691,135

[22] Filed: Aug. 1, 1996

[51] Int. Cl.$^6$ ................................................. A61K 31/65
[52] U.S. Cl. ................................................. 514/152
[58] Field of Search ................................................. 514/152

[56] References Cited

U.S. PATENT DOCUMENTS

| | | |
|---|---|---|
| 3,823,212 | 7/1974 | Chvapil . |
| 4,016,877 | 4/1977 | Cruz, Jr. et al. . |
| 4,130,555 | 12/1978 | Ohtsuka et al. . |
| 4,294,241 | 10/1981 | Miyata . |
| 4,407,787 | 10/1983 | Stemberger . |
| 4,412,947 | 11/1983 | Cioca . |
| 4,440,680 | 4/1984 | Cioca . |
| 4,578,067 | 3/1986 | Cruz, Jr. . |
| 4,666,897 | 5/1987 | Golub et al. . |
| 4,704,383 | 11/1987 | McNamara et al. ..................... 514/152 |
| 4,813,942 | 3/1989 | Alvarez . |
| 4,834,734 | 5/1989 | Morganti . |
| 4,837,024 | 6/1989 | Michaeli . |
| 4,841,962 | 6/1989 | Berg et al. . |
| 4,925,833 | 5/1990 | McNamara et al. . |
| 4,935,412 | 6/1990 | McNamara et al. ..................... 514/152 |
| 4,950,483 | 8/1990 | Ksander et al. . |
| 4,969,912 | 11/1990 | Kelman et al. . |
| 5,008,283 | 4/1991 | Blackburn, Jr et al. ................. 514/414 |
| 5,024,841 | 6/1991 | Chu et al. . |
| 5,081,106 | 1/1992 | Bentley et al. . |
| 5,110,604 | 5/1992 | Chu et al. . |
| 5,156,601 | 10/1992 | Lorenz et al. . |
| 5,196,196 | 3/1993 | Scott et al. . |
| 5,227,168 | 7/1993 | Chvapil et al. . |
| 5,240,958 | 8/1993 | Campion et al. ......................... 514/445 |
| 5,258,371 | 11/1993 | Golub et al. ............................. 514/152 |
| 5,308,839 | 5/1994 | Golub et al. ............................. 514/152 |
| 5,459,135 | 10/1995 | Golub et al. ............................. 514/152 |
| 5,532,227 | 7/1996 | Golub et al. ............................. 514/152 |

FOREIGN PATENT DOCUMENTS

| | | |
|---|---|---|
| 1767900A | 9/1971 | Germany . |
| 91/15506 | 10/1991 | WIPO . |

OTHER PUBLICATIONS

Chang et al., "Local and Systemic Factors in Periodontal Disease Increase Matrix–Degrading Enzyme Activities in Rat Gingiva: Effect of Micocycline Therapy", Research Communications in Molecular Pathology and Pharmacology, 91(3):303–318 (1996).

Clark, "Cutaneous Wound Repair," Dermal Macromolecules and Their Metabolism, 576–601 (1990).

Clark, RAF, "Biology of Dermal Wound Repair," Dermatol. Clinics 11(4):647–666 (1993).

Golub et al., "Further Evidence That Tetracyclines Inhibit Collagenase Activity in Human Crevicular Fluid and from Other Mammalian Sources," J. Periodontal Res. 20:12–23 (1985).

Golub et al., "Treating Periodontal Diseases by Blocking Tissue–Destructive Enzymes," J.A.D.A. 125:163–171 (1994).

Golub et al., "Tetracyclines Inhibit Connective Tissue Breakdown: New Therapeutic Implications for an Old Family of Drugs," Critical Reviews in Oral Biology and Medicine, 2(2):297–322 (1991).

Inoue et al., "Collagenase Expression Is Rapidy Induced in Wound–Edge Keratinocytes After Acute Injury in Human Skin, Persists During Healing, and Stops at Re–Epithelialization," The Journal of Investigative Dermatology, 104(4):479–483 (1995).

Mitscher, LA, The Chemistry of the Tetracycline Antibiotics, Ch. 6, Marcel Dekker, New York (1978).

Ramamurthy NS et al., "The Effect of Diabetes on Lysyl Oxidase Activity and Extractability of Newly Synthesized Collagen In Rat Gingiva and Skin," Gerodontology, 2:15–19 (1983).

Ramamurthy NS et al., "Endotoxin Induces MMP Mediated Bone Loss In Rat Periodontium: Inhibition of Matrix Metalloproteinases by CMT's," Journal of Dental Research, 75:105 (1996).

Ryan et al., "Matrix Metalloproteinases and Their Inhibition In Periodontal Treatment," Current Opinion in Periodontology, 3:85–96 (1996).

Stegemann, H, "Mikrobestimmung von Hydroxyprolin mit Chloramin–T und p–Dimethylaminobenzaldehyd" (A Microcolorimetric Assay for Hydroxyproline), Hoppe–Seylers Z Physiol. Chem. 311:41–45 (1958) (with English abstract).

Schneir M, N Ramamurthy, and L Golub, "Minocycline–Treatment of Diabetic Rats Normalizes Skin Collagen Production and Mass: Possible Causative Mechanisms," Matrix 10:112–123 (1990).

Zhang et al., "Chemically Modified Tetracycline (CMT–6) Applied Topically Enhances Diabetic Wound Healing," Journal of Dental Research, 75:108 (1996).

*Primary Examiner*—Raymond Henley, III
*Attorney, Agent, or Firm*—Hoffmann & Baron, LLP

[57] ABSTRACT

A method for improving the healing response of epithelialized tissue (e.g., skin, mucosae) to acute traumatic injury is disclosed. The method includes employing a tetracycline compound, having substantially no antibacterial activity, to improve the capacity of the epithelialized tissue to heal acute wounds. Specifically, the method involves increasing the rate of collagen accumulation of the healing epithelialized tissue above that associated with wound healing in the individual. The method decreases proteolytic activity in the epithelialized tissue by means of the tetracycline compound, most commonly decreasing collagenolytic activity and/or decreasing gelatinolytic activity. Collagenase and gelatinase activity have been shown to be decreased by the method of the invention. Preferably, the method is employed to improve the wound healing capacity of human or animal subjects in whom such capacity is impaired. Also, the non-antibiotic tetracycline is preferably administered topically at the site of the wound.

9 Claims, 2 Drawing Sheets

PROMOTION OF WOUND HEALING BY CHEMICALLY-MODIFIED TETRACYCLINES

This invention was made with Government support under Grant No. R37-DE-03987 awarded by the National Institutes of Health. The Government has certain rights in the invention.

BACKGROUND OF THE INVENTION

The invention relates to a method of using tetracyclines for promoting wound healing. Specifically, the invention relates to a method of using chemically-modified tetracyclines for enhancing healing of acute or non-chronic wounds in subjects in which such healing is impaired.

The medical importance of wound healing cannot be overstated. In enabling us to overcome traumatic injury, surgery, and wounds due to microbial or other physical or chemical agents, the capacity to heal is central to human well being. Classically, it has been understood that a major impediment to wound healing has been infection by bacteria or other microbes. To this end, chemical and physical barriers to infection have been conceived and implemented. Chemical barriers include general antiseptic agents and methods, pioneered by Lister and others. The chemical inhibition of microbes entered a new age with the advent of antibiotics, capable of being used topically, but also capable of administration to humans and animals by various systemic routes. Physical barriers, by contrast, do not attack the microbial elements but impair their physical access to wounds, protecting the wound from infection but also protecting against re-injury. Combined application of chemical and physical barriers has also been employed, such as incorporating an antibiotic into a wound dressing.

One particularly successful class of antibiotics is the tetracyclines. Such compounds as tetracycline, sporocycline, etc., are broad spectrum antibiotics, having utility against a wide variety of bacteria. The parent compound, tetracycline, has the following general structure:

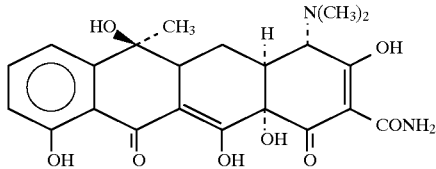

The numbering system of the multiple ring nucleus is as follows:

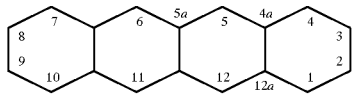

Tetracycline, as well as the 5-OH (terramycin) and 7-Cl (aureomycin) derivatives, exist in nature, and are all well known antibiotics. Natural tetracyclines may be modified without losing their antibiotic properties, although certain elements of the structure must be retained to do so. The modifications that may and may not be made to the basic tetracycline structure have been reviewed by Mitscher (1978). According to Mitscher, the modification at positions 5–9 of the tetracycline ring system can be made without causing the complete loss of antibiotic properties. However, changes to the basic structure of the ring system, or replacement of substituents at positions 1–4 or 10–12, generally lead to synthetic tetracyclines with substantially less, or essentially no, antibacterial activity. For example, 4-dedimethylaminotetracycline is commonly considered to be a non-antibacterial tetracycline.

The use of tetracycline antibiotics, while generally effective for treating infection, can lead to undesirable side effects. For example, the long term administration of antibiotic tetracyclines can reduce or eliminate healthy flora, such as intestinal flora, and can lead to the production of antibiotic resistant organisms or the overgrowth of yeast and fungi.

Antibacterial tetracyclines can be administered enterally or parenterally, but can also be applied topically as inhibitors of bacterial growth. Such compounds, and other antibiotics, have been employed in conjunction with physical barriers such as bandages.

Berg et al., in U.S. Pat. No. 4,841,962, describe a use of antibiotics and other types of chemical agents in wound dressings. For example, Berg et al. suggest that tetracycline be incorporated into a collagen matrix adhered to a dressing, for release at a wound site. The Berg et al. document, however, does not describe or suggest the use of a tetracycline for other than antibiotic uses. Also, there is no disclosure of prevention of collagen degradation in the healing of wounds.

Other examples of antibacterial agents being incorporated into wound dressings are known, e.g., U.S. Pat. No. 5,081,106 to Bentley et al., which describes collagen gelatin dressings including iodine, and U.S. Pat. No. 5,227,168 to Chvapil et al., which discloses a collagen dressing including stabilized chlorine compounds.

U.S. Pat. No. 4,950,483 to Ksander et al. illustrates a use of an implantable wound-healing matrix, formed of collagen fibrils, which can include an antibiotic or other bioactive agent such as FGF or TGF-β. Ksander et al. indicate that the matrix itself is useful for encouraging tissue repair. See also U.S. Pat. Nos. 5,024,841 and 5,110,604 to Chu et al. Other U.S. patents disclose other methods and products for implanting collagen into wounds to facilitate healing, e.g., U.S. Pat. No. 4,837,024 to Michaeli.

While the prevention of bacterial infection in wounds is important, the repair of the injured tissue is essential, since even the cleanest wound remains a wound if it is not reconstructed to form intact new tissue. The processes involved in repairing cutaneous wounds is notoriously complex. (See Clark 1993). Several distinct but overlapping processes are involved, including inflammation, new tissue formation, and remodeling of the underlying connective tissue extracellular matrix (ECM). The process of new tissue formation includes processes of reepithelialization, to quickly reestablish the skin's protective barrier against bacterial invasion, and granulation tissue formation, a multi-faceted process which occurs more deeply in the tissue and takes longer to initiate and complete.

Collagen is a major component of connective tissue matrices, not only in skin, but also in other tissues, such as bone, synovium, eye, tendons, cartilage, and gingiva. Collagen deposition and accumulation during acute wound healing begins with the onset of granulation tissue formation and continues throughout the extensive phase of matrix remodeling. However, the removal of collagen early in the wound repair process is essential to debridement of the wound and to setting the stage for proper reconstruction of the epidermis. Collagen breakdown is mediated by mammalian collagenase, a well-characterized matrix metalloproteinase, which is produced soon after a wound occurs (Inoue et al. 1995). Thus, collagenolytic activity is considered to be a normal feature of acute wound repair.

Indeed, at first glance it would appear that unusually high levels of collagen breakdown might be beneficial in the debridement and remodeling of tissues recovering from dermal insult. However, it is recognized that the production of collagenase may become excessive.

Recently, a new class of compounds has been defined which are structurally related to the antibiotic tetracyclines, but which have had their antibiotic activity substantially or completely extinguished by chemical modification. These compounds, known as chemically-modified tetracyclines (CMTs) have been found to possess a number of interesting properties, such as the inhibition of excessive collagenolytic activity in vivo. (See, for example, Golub et al. 1991; Ryan et al. 1996).

A suggestion to use CMTs in assisting in the healing of chronic wounds was made in U.S. Pat. No. 4,704,383 to McNamara et al. Therein it is stated that tetracyclines can be applied topically to skin in the treatment of ulcerative lesions such as decubitus ulcers, diabetic ulcers, and epidermolysis bullosa. Such application is related to the action of tetracyclines as inhibitors of excessive collagenase activity in conditions in which such excessive activity is found. The chronic ulcers mentioned in the McNamara et al. document are typical of those which result from or are attributable to excessive collagenolytic activity. Such ulcers do not spontaneously heal at anything approaching the normal healing rate, and often do not heal at all. Certainly, long term antibiotic usage in such conditions does not enable healing per se, underlining the point that, while microbial inhibition is an important consideration, antibiotics do not promote the underlying (host metabolic) mechanisms by which the ulcerated tissue is repaired. Moreover, while apparently useful in treating wounds resulting from excessive collagenolytic activity, it is not apparent from the McNamara et al. patent whether CMTs would have any utility in acute wounds, which are induced by other causes. Nor does this document provide any suggestion that inhibition of collagenolytic activity might be of benefit in other types of wounds.

U.S. Pat. No. 5,196,196 to Scott et al., discloses a use of protease inhibitors, secreted from connective tissue cells, in wound dressings as a means of regulating the activity of enzymes (serine proteases) involved in remodeling or destruction of tissues. Such inhibitors, however, require recombinant techniques for their identification and complex biotechnological process for their production, imparting significant expense to their preparation.

In view of the above considerations, it is clear that methods in use in the existing art for promoting healing of acute trauma wounds are limited in a number of ways. For example, the existing art does not provide efficient means for promoting physiological processes involved in the healing of acute trauma wounds such as lacerations, abrasions, and incisions.

Accordingly, it is one of the purposes of this invention to overcome the above limitations in the practice of medicine, by providing a way to promote healing of acute or non-chronic wounds.

SUMMARY OF THE INVENTION

It has now been discovered that these and other objectives can be achieved by the present invention, which provides a method for promoting wound healing in skin and other epithelialized or mucosal tissues. The method includes administering to a mammalian subject having an acute trauma wound to skin or another epithelialized tissue, a tetracycline compound in an amount which has substantially no anti-bacterial activity but which is effective to improve wound healing in the subject.

In the method of the invention, it is preferred that the tetracycline compound is substantially not absorbed systemically. Preferred tetracycline compounds include, for example, CMT-2 (tetracylinonitrile) and CMT-6 (4-hydroxy-4-dedimethylaminotetracycline). A preferred method involves administering the tetracycline compound topically to the epithelialized or mucosal tissue. Moreover, the method further includes administering the tetracycline compound and also administering an anti-inflammatory amount of a non-steroidal anti-inflammatory drug.

In a preferred case, the mammal has impaired wound healing capacity in the epithelialized tissue, and the method improves the wound healing capacity in the mammal, even up to levels at or above levels considered to be normal in the population. In this case, the impaired wound healing is typically characterized by increased proteolytic activity in the skin or other epithelialized tissue of the subject. The increased proteolytic activity can result from increased collagenolytic activity or increased gelatinolytic activity or both.

In another embodiment, the invention includes a method for increasing collagen in the connective tissue of skin or other epithelialized tissue that has been subjected to an acute trauma wound. In this embodiment, the method involves introducing to the skin or other epithelialized tissue a tetracycline compound in amount which has substantially no anti-bacterial activity but which is sufficient to increase collagen content of the epithelialized tissue to replace the collagen or connective tissue which was lost due to the trauma. The method can be used to increase collagen levels in skin or other epithelialized tissue of a subject having abnormally low levels of collagen in his or her tissue.

The invention further provides a wound dressing for promote healing of an acute trauma wound to skin or other epithelialized tissue. The wound dressing includes: a support base, and a tetracycline compound in an amount which has substantially no anti-bacterial activity but which is sufficient to promote healing in the epithelialized tissue. The wound dressing can also include a non-steroidal anti-inflammatory drug in an amount sufficient to inhibit inflammation in the epithelialized tissue.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawing, wherein.

DETAILED DESCRIPTION OF THE PREFERRED EMBODIMENTS

Figure 1:
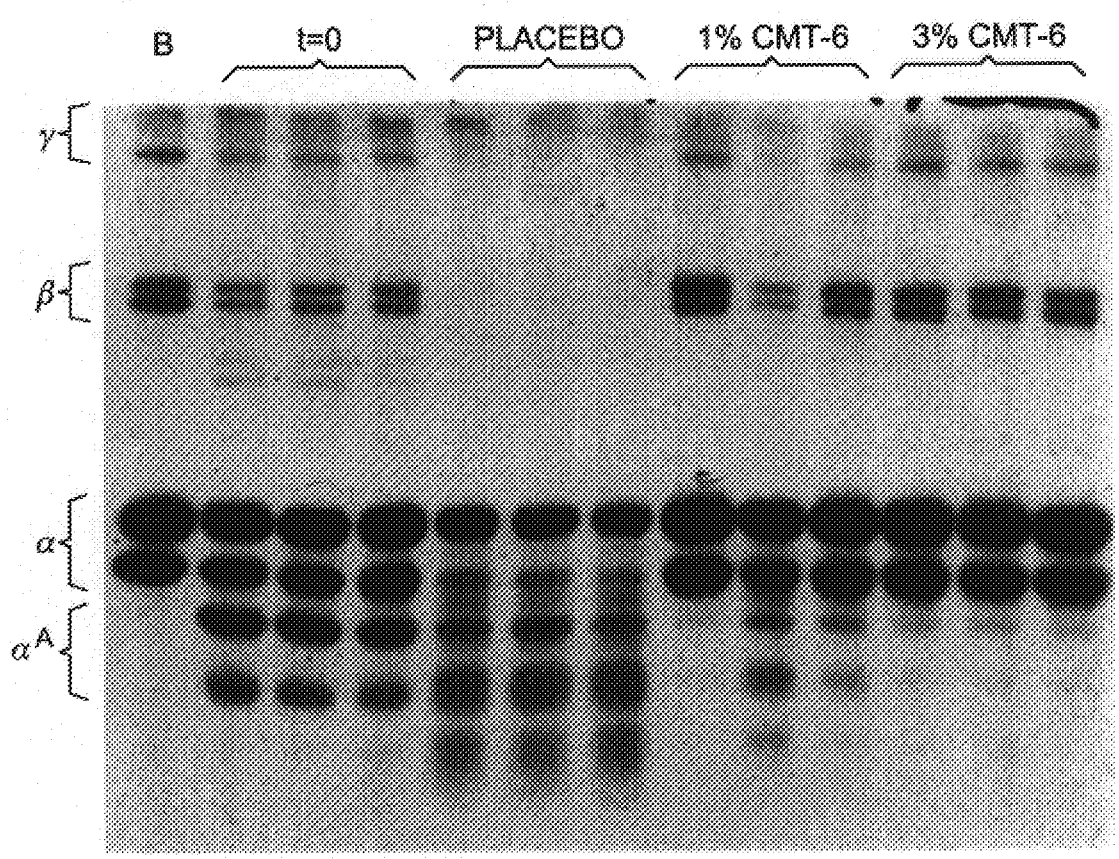
FIG. 1 is a computer scan of a PAGE gel showing the effect of a tetracycline (CMT-6) treatment on collagenase activity in the healing wound assessed using [$^3$H-methyl] collagen as substrate.

The present invention is directed to the promotion of healing of acute trauma wounds in epithelialized tissues. The method of the invention includes administering tetracycline compounds to restore or improve healing of acute trauma wounds to the skin and other epithelialized tissues. The tetracycline compounds are preferably chemically modified tetracyclines, which generally have little or no antimicrobial capacity. However, sub-antibacterial doses of typically antibacterial tetracyclines can also be given according to the invention.

The method of the invention is adapted to be used for the promotion of healing of acute trauma wounds in mammals. Acute trauma wounds are typically of sudden onset, such as lesions produced in a traumatic injury. The class of wounds susceptible to treatment according to the invention includes acute trauma wounds which heal by first intention and acute trauma wounds which heal by second intention. Thus, the method is useful in improving healing of wounds which heal by first intention, which are characterized by healing of the wound without intervention of granulations. Such wounds are typified by surgical incisions. The method is also useful in assisting healing of wounds which heal by second intention, i.e., wounds in which healing is characterized by the formation of granulations. Wounds of second intention are exemplified by lacerations, punctures, abrasions, and the like. The acute trauma wounds treatable according to the invention may also be designated as "non-chronic" wounds.

Wounds generally classified as "chronic," or of long-standing duration and/or spontaneous or non-traumatic origin, are outside the scope of the invention. For example, the invention does not involve treatment of ulcerative lesions or erosions, such as decubitus ulcers (bed sores), diabetic ulcers, epidermolysis bullosa, and sterile corneal ulcers, or the like.

The method promotes healing of incised, lacerated, perforated, or abraded skin (cutis) in the subject being treated. Epidermal, dermal and underlying subcutaneous tissues can be involved in such acute cutaneous or mucosal wounds, and healing can be improved in any or all of these tissue types by means of the invention. Also, the method can be used to improve healing in other epithelialized tissues, such as any tissue in which an epithelial layer is injured, either with or without injury to underlying supportive or connective tissues. The term "epithelialized tissue" is generally applied herein to refer to skin and any other tissues having or associated with an epithelium (as the latter term is used conventionally). Other tissues within the meaning of the term "epithelialized tissues" and, therefore, suitable for treatment according to the invention, include, without limitation, mucosal tissues in the oral cavity and other body cavities. Functionally, the method is useful in treating any acutely traumatized body tissue in which the inhibition of collagenolytic activity is of benefit in improving healing of the tissue.

The conditions treatable by means of the present invention occur in mammalian subjects. Mammals include, for example, humans, as well as pet animals such as dogs and cats, laboratory animals such as rats and mice, and farm animals, such as horses and cows.

Among the benefits of the method of the invention is that it can be used to improve the integrity of healing skin by reducing the amount of granulation during the healing process. Granulation is characterized by the formation in wounds of small, rounded masses of tissue composed largely of capillaries and fibroblasts, often with inflammatory cells present. Thus, excessive cicatricial tissue can be reduced, accompanied by lessened disfigurement or distortion of the skin associated with scarring.

The method involves the administration of a tetracycline compound in an amount which has substantially no antibacterial activity, but which is effective for improving healing of an acute trauma wound in an epithelialized tissue. Preferably the tetracycline compound has been modified chemically to reduce or eliminate its antimicrobial properties. Methods for reducing the antimicrobial properties of tetracyclines were disclosed in Mitscher (1978). As pointed out by Mitscher, modification of tetracycline at positions 1, 2, 3, 4, 10, or 12a leads to loss of antibiotic activity. The use of such chemically-modified tetracyclines is preferred in the present invention since they can be used at higher levels than antimicrobial tetracyclines, while avoiding certain disadvantages, such as the indiscriminate killing of beneficial microbes, and the emergence of resistant microbes, which often accompanies the use of antimicrobial or antibacterial amounts of such compounds.

The preferred chemically-modified tetracyclines are those which lack the dimethylamino group at position 4 of the ring structure. Such chemically-modified tetracyclines include, for example, 4-dedimethylaminotetracycline (CMT-1), 4-dedimethylamino-5-oxytetracycline, 4-dedimethylamino-7-chlorotetracycline (CMT-4), 4-hydroxy-4-dedimethylaminotetracycline (CMT-6), 5a,6-anhydro-4-hydroxy-4-dedimethylaminotetracycline, 6-demethyl-6-deoxy-4-dedimethylaminotetracycline (CMT-3), 4-dedimethylamino-12a-deoxytetracycline (CMT-7), and 6-a-deoxy-5-hydroxy-4-dedimethylaminotetracycline (CMT-8). Also, tetracyclines modified at the 2 carbon position to produce a nitrile, e.g., tetracyclinonitrile, are useful as non-antibacterial, anti-metalloproteinase agents.

Further examples of tetracyclines modified for reduced antimicrobial activity include 6-α-benzylthiomethylenetetracycline, the mono-N-alkylated amide of tetracycline, 6-fluoro-6-demethyltetracycline, or 11α-chlorotetracycline.

A particularly preferred CMT is 4-hydroxy-4-dedimethylaminotetracycline (herein designated CMT-6), which has been found to significantly improve collagen content in healing wounds. Another highly preferred CMT is tetracyclinonitrile (CMT-2), which appears to be even more effective in promoting healing. Indeed, CMT-2 and CMT-6 are not substantially absorbed into the bloodstream when ingested, and are generally limited in their biodistribution. CMT-2, CMT-6, and other CMTs exhibiting such substantially local distribution are preferred for their localized efficacy in inhibiting collagenolytic activity at a site of injury, without exhibiting broader systemic inhibition of proteolytic activity. For example, the topical application of these non-absorbable CMTs would be desirable in oral lesions, since the CMTs would not be absorbed to any significant degree even if swallowed.

The invention can also use tetracycline compounds which possess antibacterial activity. However, such compounds are employed in an amount which has substantially no antibacterial effect but which is effective for improving healing of the acute trauma wound in the epithelialized tissue. Preferred compounds of this type include tetracycline, doxycycline, demeclocycline, and minocycline.

The tetracycline compounds useful according to the method of the invention appear to exhibit their beneficial effect in a dose-dependent manner. Thus, within broad limits, administration of larger quantities of a tetracycline compound has been observed to improve wound healing to a greater degree than does administration of a smaller amount. Moreover, efficacy has been observed at dosages below the level at which toxicity is seen.

The amount of the tetracycline compound used according to the invention is an amount that is effectively anti-collagenolytic, while not being effectively antimicrobial. An amount of a tetracycline compound is effectively anti-collagenolytic if it significantly reduces collagenolytic activity. A tetracycline compound is not effectively antimicrobial if it does not significantly prevent the growth of microbes.

The maximal dosage for a subject is the highest dosage which does not cause undesirable or intolerable side effects. For example, the tetracycline compound can be administered in an amount of from about 0.1 mg/kg/day to about 30 mg/kg/day, and preferably from about 1 mg/kg/day to about 18 mg/kg/day. For the purpose of the present invention, side effects include clinically significant antimicrobial or anti-bacterial activity, as well as toxic effects. For example, a dose in excess of about 50 mg/kg/day would likely produce side effects in most mammals, including humans. In any event, the practitioner is guided by skill and knowledge in the field, and the present invention includes without limitation dosages which are effective to achieve the described phenomena.

Topical application of tetracycline compounds in amounts of up to about 25% (w/w) in a vehicle are therefore appropriate depending upon indication. More preferably, application of tetracycline compounds in amounts of from about 0.1% to about 10% is believed to effectively promote healing according to the invention. It is believed that these quantities do not induce significant toxicity in the subject being treated.

Combined or coordinated topical and systemic administration of tetracycline compounds is contemplated under the invention. For example, a non-absorbable tetracycline compound, such as CMT-2 or CMT-6, can be administered topically, while a tetracycline compound capable of substantial absorption and effective systemic distribution in the subject, such as CMT-1, CMT-3, CMT-7, or CMT-8, is administered systemically.

The tetracycline compound can also be administered with an agent capable of inhibiting inflammation in tissue subjected to an acute trauma wound. Preferred anti-inflammatory agents capable of co-administration include non-steroidal anti-inflammatory drugs (NSAIDs). The NSAID can be selected from the various classes of such compounds. Such classes include, for example, salicylates such as acetylsalicylic acid and diflunisal; acetic acids such as indomethacin, sulindac, tolmetin, diclofenac, and etodolac; propionic acids such as flurbiprofen, naproxen, and ketoprofen; and fenamates such as meclofenamate; and oxicams such as piroxicam. Generally, the amount of the NSAID is an amount sufficient to inhibit inflammation in the affected tissue. The anti-inflammatory amount will depend on the NSAID being employed and other understood factors, and can be readily determined by the skilled practitioner.

The preferred pharmaceutical composition for use in the method of the invention comprises a combination of the tetracycline compound in a suitable pharmaceutical carrier (vehicle) or excipient as understood by practitioners in the art. A highly preferred means of delivery includes topical application. Accordingly, the carrier is preferably suited for topical use. Compositions deemed to be suited for such topical use include as gels, salves, lotions, ointments and the like. The non-antimicrobial amount of the tetracycline compound may be incorporated with a support base or matrix or the like to provide a pre-packaged surgical or burn dressing or bandage which can be directly applied to a wound. Such dressings can be employed with or without application of facilitating pharmaceutically acceptable substances such as antibiotic creams. Time-release or controlled-delivery administration may be employed, e.g., by applying the tetracycline compound with a biocompatible polymer co-formed into a fibrous material. Indeed, resorbable collagen matrices are suited for time-release delivery of medicaments (see, e.g., U.S. Pat. Nos. 4,440,680 to Cioca; 4,407,787 to Stemberger; and 4,294,241 to Miyata), and can be employed to deliver tetracycline compounds according to the present invention. Optionally, a non-tetracycline antibiotic compound may be included with the nonmicrobial amount of the tetracycline compound and the carrier to inhibit microbial growth at the site of the wound. Alternatively, the means of delivery of the tetracycline compound with the pharmaceutical carrier may be in the form of a capsule, compressed tablet, pill, solution, or suspension suitable for oral administration to the subject. Contemplated compositions include those which are formulated with carriers suitable for administration orally, topically, by injection, or by other means.

The method of the invention increases the rate of collagen accumulation in healing epithelialized tissue. Accordingly, the invention increase the rate of healing of acute trauma wounds by inhibiting mammalian matrix metalloproteinases (MMPs), especially collagenase and gelatinase, thereby decreasing the rate of collagen breakdown in the healing tissue. (It is possible that the observed rate of increase in collagen content reflects, in part, increased collagen synthesis and/or secretion.) Tetracycline compounds appear to inhibit neutrophil collagenase, as well as fibroblast collagenase. For example, Chang et al. (1996) have shown that diabetes is associated with increased amounts of leukocyte-type collagenase and gelatinase in skin, presumably produced by (cytokine-stimulated) fibroblasts. Accordingly, the method of the invention is believed to effectively increase healing of acute trauma wounds by inhibiting fibroblast collagenase, which is normally active in tissue remodeling, or neutrophil leukocyte collagenase, an enzyme which is typically active in the early stages of wound healing, tearing down injured tissue at the time inflammation is occurring. The method is particularly applicable to the inhibition of neutrophil type collagenase.

Also, because the neutrophil collagenase and fibroblast collagenase are generated at the site of injury at different times, it is within the scope of the invention to provide a time-based regimen including a sequence of two or more specifically-acting tetracycline compounds, such as for the inhibition of neutrophil collagenase earlier in the healing process, with the inhibition of fibroblast collagenase later. Alternatively, a derangement in the expression of a single type of collagenolytic activity in certain individuals could indicate the application of a regimen directed to inhibiting that single source of activity.

The method is particularly applicable to subjects in whom the healing process is impaired. For example, in cases in which the levels of collagenase rise in response to an acute trauma injury, but which do not fall again as they normally would, the injury can become chronic, taking an excessively long time to heal. The method of the invention can be used to overcome the failure of the skin to reduce the level of collagenolytic activity, thereby permitting an increase in collagen deposition and concomitant normalized healing, and preventing the induction of a chronic lesion.

Thus, the method of using chemically-modified tetracyclines according to the invention is useful in persons having acute or chronic impairment of wound healing, most especially in persons suffering from diabetes. It is known that impaired wound healing is one of the many complications of poorly controlled diabetes mellitus. Several diabetes-induced abnormalities in the metabolism of collagen have been identified, including pathologically excessive collagenase and gelatinase in the gingiva and skin of the streptozotocin-diabetic rat (Ramamurthy et al. 1983; Chang et al. 1996). We have now shown that such abnormalities can be effectively inhibited, leading to the restoration of healing of acute wounds in persons suffering from such conditions.

The following examples are provided to assist in a further understanding of the invention. The particular materials and conditions employed are intended to be further illustrative of the invention and are not limiting upon the reasonable scope thereof.

EXAMPLE 1

Adult male Sprague-Dawley rats (approx. 350 g body weight) were distributed into the following experimental groups:

Group I (n=4 rats): non-diabetic controls treated with vehicle alone (NDC group);

Group II (n=3 rats): uncontrolled diabetics treated with vehicle alone (D group); and Group III (n=3 rats): diabetics treated topically with CMT-6 (1% suspension in a mineral oil-based petrolatum vehicle).

At the beginning of the experiment (T=0), the appropriate numbers of rats were administered streptozotocin (STZ) (70 mg/kg) by intravenous injection by the tail vein, to induce diabetes and hyperglycemia according to the method established by Yu et al. (1993). Then 21 days after STZ injection, all of the rats were anesthetized, and six circular fill-thickness wounds were created with a 6 mm diameter biopsy punch in the dorsal skin of each rat (the wounds were allowed to heal by secondary intention). Beginning on the day the wounds were created, the petrolatum vehicle, either alone or containing CMT-6, was applied once per day for seven days.

At the end of the seven-day period, the wounds were surgically dissected and examined, both histologically and biochemically. For the former analysis, the skin biopsies were stored in 10% neutral-buffered formalin, then sectioned and stained with Mason trichrome, which stains collagen fibers (the major structural constituent of the dermal connective tissue) a blue color. For the latter examination, the skin biopsies were dried at 37° C., weighed, and then hydrolyzed in 6 M HCl (106° C., 24 hr, in a sealed test tube) to break down the collagen protein to its constituent amino acids, and then calorimetrically analyzed for hydroxyproline, which is an amino acid "marker" of collagen, according to the method of Stegmann (1958).

In all three groups of rats, the epithelium appeared to be completely reconstituted over the healing dermis by day 7 following creation of the wound. The results of these assays are summarized in Table 1. Trichrome staining is expressed qualitatively, and hydroxyproline content in the skin samples is expressed as $\mu$g/mg dry tissue (±standard error of the mean).

Samples of healing skin, stained as directed to illustrate collagen content, were subjected to microscopic analysis (confirmed by photomicrography). A micrograph of the healing skin of a normal rat (Group I), showed dense staining for collagen. By contrast, a micrograph of healing skin from an untreated diabetic rat (Group II), showed only very light staining for collagen, illustrative of the impairment of healing is these animals. Finally, a micrograph of healing skin from a diabetic rat treated with 1% CMT-6 as described (Group III), showed collagen content in the skin which is significantly increased over that found in the untreated diabetic rats. These data are summarized qualitatively in Table 1

TABLE 1

| Experimental Group | Collagen Content at Day 7 | |
|---|---|---|
| | Histology | Hydroxyproline ($\mu$g/mg) |
| I: Normal | ++++ | 29 ± 6 |
| II: Untreated diabetic | + | 20 ± 3 |
| III: Diabetics with 1% CMT-6 | +++ | 25 ± 7 |

As shown in Table 1, making the rats diabetic reduced the collagen content of the healing wound as compared with normal controls. This conclusion was based on a 31% reduction in hydroxyproline content, and based on a reduction in trichrome blue staining of the collagen fibers, compared to the NDC group. Nonetheless, the Group III rats (diabetic plus CMT-6) showed collagen content of the healing skin which was 25% increased over the untreated diabetics based on hydroxyproline measurements, which in turn was consistent with increased trichrome staining of collagen based on histologic observation.

EXAMPLE 2

An experiment similar to that described in Example 1 was performed, except that two concentrations of CMT-6 were suspended in the mineral oil base petrolatum vehicle, i.e., suspensions of 1% and 3% CMT-6 were tested. In this case, 21 adult male rats were distributed into 4 experimental groups:

Group I (n=4 rats): non-diabetic controls (NDC) treated daily by topical application of vehicle alone;

Group II (n=5 rats): uncontrolled diabetics (D) treated as above with vehicle alone;

Group III (n=6 rats): uncontrolled diabetics treated daily with 1% CMT-6 in petrolatum; and Group IV (n=6 rats): uncontrolled diabetics treated daily with 3% CMT-6 in petrolatum.

As in Example 1, after a 7-day protocol, the rats were anesthetized, biopsies of skin were excised, hydrolyzed, and analyzed colorimetrically for hydroxyproline content. The results of this analysis are presented in Table 2, wherein the hydroxyproline content is expressed as $\mu$g of hydroxyproline/mg of dry tissue (±S.E.M.)

TABLE 2

| Experimental group | Hydroxyproline content of skin |
|---|---|
| I: Non-diabetic controls | 25 ± 2 |
| II: Untreated diabetics | 19 ± 2 |
| III: Diabetics with 1% CMT-6 | 27 ± 6 |
| IV: Diabetics with 3% CMT-6 | 33 ± 11 |

In this experiment, inducing diabetes reduced the collagen content of the healing skin in the Group II animals below control (Group I) levels by 24% (Table 2). However, treating diabetic rats by topical administration of 1% CMT-6 (Group III) and 3% CMT-6 (Group IV) increased the wound collagen content by 42% and 74%, respectively, over the untreated diabetics (Group II). This clearly indicates a dose-response effect on the wound healing.

EXAMPLE 3

In this experiment, adult male rats were distributed into four different experimental groups, with n=4–6 rats per group:

Group I: Diabetics with vehicle alone;
Group II: Diabetics with 1% CMT-6;
Group III: Diabetics with 3% CMT-6; and
Group IV: Diabetics with 1% CMT-2.

The wounding protocol developed as described above was employed. On day 7 following wounding, and after daily topical application of either vehicle alone or CMT-6 or CMT-2, the wounds were surgically excised, and collagenase activity was measured according to the method of Golub et al. (1985).

In brief, collagenase activity was measured as follows: each skin biopsy was weighed, extracted, and the extracts partially purified by ammonium sulfate precipitation. Aliquots of the skin extracts were then incubated with [$^3$H-methyl] collagen at 22° C., and the reaction products were separated by SDS-PAGE/fluorography. The fluorograms were then scanned by a laser densitometer to assess collagenase activity. (This assay was carried out in the absence of aminophenylmercuric acetate (APMA), to assess active, not latent, collagenase, as described by Golub et al. (1994).)

FIG. 1 shows the electrophoretic pattern of [$^3$H-methyl] collagen after incubation with skin extracts from the diabetic rats from Groups I–III. Lanes 2–4: t=0; lanes 5–7: placebo (vehicle alone); lanes 8–10: 1% CMT-6; and lanes 11–13: 3% CMT-6. Lane 1 is a control sample of collagen with no skin extract, showing the pattern of undegraded collagen including the α, β, and γ collagen components. Note the high collagenase activity in the diabetic rat skin at t=0 ($\alpha^A$ fragments) (lanes 2–4) which is even higher in the placebo-treated (vehicle-treated) skin of the diabetics (lanes 5–7). Treatment with CMT-6 decreased excess collagenase activity, as indicated by (i) decreased loss of α, β, and γ collagen components, and (ii) decreased formation of $\alpha^A$ collagenase-mediated breakdown products. A dose-dependent effect of CMT-6 is evident (lanes 8–13).

Figure 2:
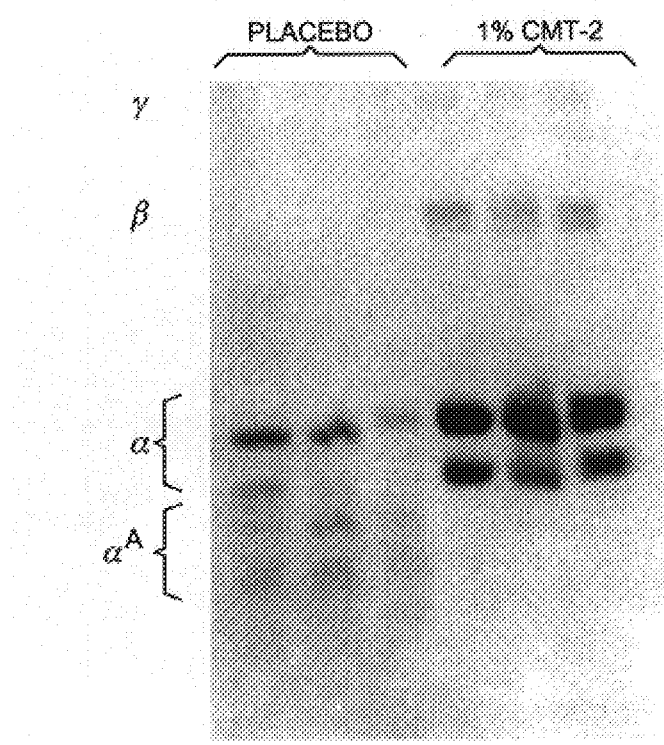
FIG. 2 is a fluorogram of a PAGE gel showing the effect of a tetracycline (CMT-2) treatment on collagenase activity in the healing wound assessed using [$^3$H-methyl] collagen as substrate.

FIG. 2 shows the electrophoretic pattern of [$^3$H-methyl] collagen after incubation with skin extracts from placebo (vehicle-treated) diabetic rats (lanes 1–2) and from 1% CMT-2-treated diabetic rats (lanes 3–5). As in FIG. 1 above, a high level of collagenase activity is seen in the placebo-treated skin, while a most dramatic inhibition of collagenase activity by CMT-2 is also evidenced.

The breakdown of the radiolabelled [$^3$H-methyl] collagen by the skin extracts revealed large molecular weight fragments ($\alpha_1^A$ and $\alpha_1^A$) of collagen characteristically produced by mammalian collagenase. The results of this analysis are presented in Table 3.

TABLE 3

| Experimental group | Collegenase activity (% $^3$H-collagen degraded) |
|---|---|
| I: Untreated diabetics | 47.4 ± 0.6 |
| II: Diabetics with 1% CMT-6 | 8.3 ± 0.5 |
| III: Diabetics with 3% CMT-6 | 6.4 ± 4.3 |
| IV: Diabetics with 1% CMT-2 | 0 ± 0 |

Densitometric scanning of the fluorograms (FIGS. 1 and 2, Table 3) indicated that 47% of the [$^3$H] collagen substrate was degraded by the skin samples from the vehicle-treated diabetic rats. Treatment of the diabetic rats with 1% or 3% CMT-6, or with 1% CMT-2, all substantially reduced this high collagenase activity. Specifically, 1% CMT-6 reduced collagenolytic activity in the diabetic rats by 83%; 3% CMT-6 reduced the activity by 87%, and 1% CMT-2 reduced the activity by 100%. (In a separate experiment (data not shown), non-diabetic control rat skin at day 7 showed about 19% degradation of collagen, compared to the 47% level of degradation exhibited by the diabetic group in this experiment, and the topical application of 3% CMT-6 did not significantly (p>0.05) reduce collagenolytic activity in the NDC rat skin.)

EXAMPLE 4

Further to the experiments described above, a study was made of the effect of CMT-6 upon collagenase and gelatinase activity in normal and SZT-diabetic rats. Twenty-four rats were divided into six experimental groups:

I: Normal (n=4 rats) treated with the petrolatum vehicle only;
II: Normal (n=3 rats) treated with 3% CMT-6;
III: Diabetic (n=6 rats) untreated, tested at time=0;
IV: Diabetic (n=4 rats) vehicle only, tested at time=7 days;
V: Diabetic (n=4 rats) treated with 1% CMT-6; and
VI: Diabetic (n=3 rats) treated with 3% CMT-6.

The rats were treated according to the protocol described above, with the exception of the rats in Group III, which were tested on the day the wounds were created. Tissue biopsies were divided in half, with half being used to extract collagenase and gelatinase, and the other half being used to assay for collagen content. Collagen content and collagenase activity were assayed using the protocols described above. Gelatinase activity was assessed using denatured collagen (gelatin) as substrate. Radiolabeled [$^3$H-methyl] gelatin substrate was incubated with the extracted enzyme at 37° C. for 4 hr. The undigested gelatin was precipitated by the addition of non-labeled gelatin, and 45% TCA. After centrifugation, the supernatants containing the gelatin degradation products were counted in a liquid scintillation spectrometer.

The two MMPs (collagenase and gelatinase) were assessed both in the absence of activation by APMA and with incubation of the enzyme extracts with APMA. The results without activation are described in Table 4, below. Collagenase activity is expressed as the rate of collagen breakdown, i.e., ng collagen degraded/hr/mg protein (±S.E.M.). Gelatinase activity is expressed as the rate of gelatin breakdown, i.e., μg gelatin degraded/hr/mg protein (±S.E.M.).

TABLE 4

| Experimental group | Collagenase | Gelatinase |
|---|---|---|
| Normal | 138 ± 18 | 0.6 ± 0.2 |
| Normal + 3% CMT-6 | 84 ± 50 | 0.3 ± 0.1 |
| Diabetics(Day = 0) | 333 ± 48 | 1.7 ± 0.1 |
| Diabetics(Day = 7) | 330 ± 41 | 1.1 ± 0.1 |
| Diabetics + 1% CMT-6 | 48 ± 29 | 0.8 ± 0.1 |
| Diabetics + 3% CMT-6 | 38 ± 20 | 0.4 ± 0.1 |

As shown in Table 4, both collagenase and gelatinase levels were elevated in the vehicle-treated diabetic wound tissues. Essentially all (90–95%) of the MMPs in the extracts were active, and very little was APMA-activatable or latent. Scanning of the fluorogram revealed 48% of collagen was degraded by the diabetic rat tissues. At time=0, the diabetic rat skin tissues also contained active collagenase and active gelatinase. In wounds treated with 1% or 3% CMT-6, collagenase and gelatinase levels were reduced in a dose-dependent manner. Normal rat skin showed no collagenase activity at time=0. However, wounding of the non-diabetic rat skin induced an increased collagenase activity (17% collagen degraded) and treating the wounds with 3% CMT-6 significantly reduced the active gelatinase (P<0.05) but reduced collagenase to a degree which was not significant.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

BIBLIOGRAPHY

Chang, K-M, M E Ryan,, L M Golub,, N S Ramamurthy,, and T F McNamara, "Local and systemic factors in periodontal disease increase matrix-degrading enzyme activities in rat gingiva: Effect of minocycline activity," *Res. Commun. Mol. Pathol. and Pharmacol.* 91(3):303–318 (1996).

Clark, R A F, "Biology of dermal wound repair", *Dermatol Clinics* 11(4):647–666 (1993).

Golub et al., *J Periodontal Res.* 20:12 (1985).

Golub, L M, N S Ramamurthy, T F McNamara, R A Greenwald, and B R Rifkin, "Tetracyclines inhibit connective tissue breakdown: New therapeutic implications for an old family of drugs", *Crit. Rev. in Oral Biol andMed.* 2(2):297–322 (1991).

Golub et al., *J.A.D.A.* 125:163 (1994).

Inoue, M, G Kratz, A Haegerstrand, and M Ståhle-Bäackdahl, "Collagenase expression is rapidly induced in wound-edge keratinocytes after acute injury in human skin, persists during healing, and stops at re-epithelialization", *J Invest. Dermatol.* 104(4):479–483 (1995).

Mitscher, L A, *The Chemistry of the Tetracycline Antibiotics,* Ch. 6, Marcel Dekker, New York (1978).

Ramamurthy, N S, L M Golub, and M Leung, "The effect of diabetes on lysyl oxidase activity and extractability of newly synthesized collagen in rat gingiva and skin," *Gerodontology* 2:15–19 (1983).

Ryan, M E, N S Ramamurthy, and L M Golub, "Matrix metalloproteases and their inhibition in periodontal treatment," *Curr. Opin. Periodontol.* 3:85–96 (1996).

Stegmann, H, "A microcolorimetric assay for hydroxyproline", *Hoppe-Seylers Z Physiol Chem.* 311:41–45 (1958).

What is claimed is:

1. A method for promoting wound healing, wherein said method comprises:

a) topically administering a first tetracycline compound to a mammal having an acute trauma wound, said first tetracycline compound being substantially incapable of systemic distribution in said mammal; and b) systemically administering a second tetracycline compound to said mammal, said second tetracycline compound being capable of substantial systemic distribution in said mammal.

2. A method according to claim 1, wherein said method further comprises administering to said mammal an anti-inflammatory amount of a non-steroidal anti-inflammatory drug.

3. A method according to claim 1, wherein said epithelialized tissue is skin.

4. A method according to claim 1, wherein said mammal has impaired wound healing capacity.

5. A method according to claim 4, wherein said impaired wound healing is characterized by increased proteolytic activity in the epithelialized tissue of the mammal.

6. A method according to claim 5, wherein the increased proteolytic activity comprises increased collagenolytic activity or increased gelatinolytic activity or both.

7. A method according to claim 4, wherein said mammal is diabetic.

8. A method according to claim 1, wherein said first tetracycline compound is CMT-2 or CMT-6.

9. A method according to claim 1, wherein said second tetracycline compound is CMT-1, CMT-3, CMT-7, or CMT-8.

* * * * *

UNITED STATES PATENT AND TRADEMARK OFFICE
CERTIFICATE OF CORRECTION

PATENT NO. : 5,827,840
DATED : October 27, 1998
INVENTOR(S) : Ramamurthy et al.

Page 1 of 2

It is certified that error appears in the above-indentified patent and that said Letters Patent is hereby corrected as shown below:

| | |
|---|---|
| In Column 6, Line 28, | delete "6-a-deoxy", and insert therefor --6-α-deoxy--. |
| In Column 9, Line 33, | delete "circular fill-thickness", and insert therefor --circular full-thickness--. |
| In Column 9, Line 48, | delete "HCI", and insert therefor --HC1--. |
| In Column 9, Line 60, | delete "as directed to", and insert therefor --as described to--. |
| In Column 10, Line 5, | delete " : Table 1", and insert therefor --Table .-- |
| In Column 10, Line 46, | delete "(±S.E.M.)", and insert therefor --(±S.E.M.).--. |
| In Column 11, Line 45, | delete "($\propto_1^A$ and $\propto_1^A$)", and insert therefor --($\propto_1^A$ and $\propto_2^A$)--. |
| In Column 13, Line 16, | delete "Dermatol Clinics", and insert therefor --Dermatol. Clinics--. |
| In Column 13, Line 17, | delete "J Periodontal Res.", and insert therefor --J. Periodontal Res.--. |
| In Column 13, Line 22, | delete "Oral Biol andMed.", and insert therefor --Oral Biol. and Med.--. |

UNITED STATES PATENT AND TRADEMARK OFFICE
CERTIFICATE OF CORRECTION

PATENT NO.   :   5,827,840  Page 2 of 2
DATED         :   October 27, 1998
INVENTOR(S) :   Ramamurthy et al.

It is certified that error appears in the above-indentified patent and that said Letters Patent is hereby corrected as shown below:

<u>In Column 13, Line 26,</u>    delete "äackdahl,", and insert therefor --Bäckdahl,--.

<u>In Column 13, Line 28,</u>    delete "J Invest.", and insert therefor --J. Invest.--.

<u>In Column 14, Line 2,</u>     delete "Z Physiol", and insert therefor --Z Physiol.--.

Signed and Sealed this

Twentieth Day of July, 1999

Attest:

Q. TODD DICKINSON

*Attesting Officer*      Acting Commissioner of Patents and Trademarks